US012332643B2

(12) United States Patent
Karri et al.

(10) Patent No.: US 12,332,643 B2
(45) Date of Patent: Jun. 17, 2025

(54) VIRTUAL FENCING OF A CONTAMINATED AREA

(71) Applicant: International Business Machines Corporation, Armonk, NY (US)

(72) Inventors: Venkata Vara Prasad Karri, Visakhapatnam (IN); Shailendra Moyal, Pune (IN); Akash U. Dhoot, Pune (IN); Sarbajit K. Rakshit, Kolkata (IN)

(73) Assignee: International Business Machines Corporation, Armonk, NY (US)

(*) Notice: Subject to any disclaimer, the term of this patent is extended or adjusted under 35 U.S.C. 154(b) by 103 days.

(21) Appl. No.: 17/651,282

(22) Filed: Feb. 16, 2022

(65) Prior Publication Data

US 2023/0259126 A1 Aug. 17, 2023

(51) Int. Cl.

| | |
|---|---|
| ***G05D 1/00*** | (2024.01) |
| ***B64U 10/13*** | (2023.01) |
| ***G01N 33/00*** | (2006.01) |
| *B64U 101/30* | (2023.01) |

(52) U.S. Cl.

CPC ........... *G05D 1/0027* (2013.01); *B64U 10/13* (2023.01); *G01N 33/00* (2013.01); *G05D 1/0094* (2013.01);

(Continued)

(58) Field of Classification Search

CPC .. G05D 1/0027; G05D 1/0094; B64C 39/024; B64U 10/00–10/80;

(Continued)

(56) References Cited

U.S. PATENT DOCUMENTS

| | | |
|---|---|---|
| 10,096,005 B2 | 10/2018 | Gordon |
| 10,820,574 B2 | 11/2020 | Gordon |

(Continued)

FOREIGN PATENT DOCUMENTS

| | | |
|---|---|---|
| DE | 102018121401 A1 | 3/2020 |

OTHER PUBLICATIONS

Disclosed Anonymously et al, "Real-Time Interaction Based Placement of Drones and Reinforcement Learning for Human and Animal Population Deterrence within Proximity to Danger", IP.com Prior Art Database Technical Disclosure, IPCOM000264979D, Feb. 12, 2021, 6 Pgs.

Seiber et al., "Tracking Hazardous Aerial Plumes using IoT-Enabled Drone Swarms", IEEE Transactions on Multimedia, 978-1-4673-9944-9/18 © 2018, 6 Pgs.

*Primary Examiner* — Anne Marie Antonucci
*Assistant Examiner* — Patrick M Brady
(74) *Attorney, Agent, or Firm* — Randy Tejeda

(57) ABSTRACT

An approach for a computer program to retrieve historical incident data associated with a contaminated site to predict a future incident at the contaminated site. In the approach, the computer program evaluates the historical incident data to determine a deployment of a plurality of unmanned vehicles to form a virtual fence around the contaminated site. Furthermore, in the approach, the computer program determines instructions for the deployment of each of the plurality of unmanned vehicles to form the virtual fence around the contaminated site. In the approach, the computer program sends the instructions to form the virtual fence to each of the plurality of unmanned vehicles.

20 Claims, 6 Drawing Sheets

(52) U.S. Cl.
CPC ...... *B64U 2101/30* (2023.01); *B64U 2201/20* (2023.01)

(58) Field of Classification Search
CPC ......... B64U 20/00–20/98; B64U 30/00; B64U 30/10–30/16; B64U 30/20–30/299; B64U 40/00–40/20; B64U 50/00–50/39; B64U 60/00–60/70; B64U 70/00–70/99; B64U 80/00–80/86; B64U 2201/20; B64U 2101/00; B64U 2101/05; B64U 2101/10; B64U 2101/15–2101/19; B64U 2101/20–2101/24; B64U 2101/25–2101/29; B64U 2101/30–2101/32; B64U 2101/35; B64U 2101/40; B64U 2101/45–2101/47; B64U 2101/55–2101/58; B64U 2101/60–2101/69; B64U 2101/70; B64U 2101/75; G01N 33/00
See application file for complete search history.

(56) References Cited

U.S. PATENT DOCUMENTS

| | | | | |
|---|---|---|---|---|
| 11,172,339 | B1 * | 11/2021 | Hummer | B64C 39/024 |
| 2005/0051065 | A1 * | 3/2005 | Hierholzer | F23G 5/40<br>110/341 |
| 2006/0184292 | A1 * | 8/2006 | Appleby | F41H 13/00<br>701/2 |
| 2016/0018559 | A1 * | 1/2016 | Levien | B63B 35/00<br>73/864.31 |
| 2018/0027772 | A1 * | 2/2018 | Gordon | A01K 1/0029 |
| 2018/0164080 | A1 * | 6/2018 | Chi-Hsueh | G01S 13/88 |
| 2019/0204189 | A1 * | 7/2019 | Mohr, Jr | G01N 21/00 |
| 2020/0309756 | A1 * | 10/2020 | Do | G05D 1/106 |
| 2020/0314587 | A1 | 10/2020 | Gurin | |
| 2021/0052930 | A1 * | 2/2021 | Lacaze | A62D 3/30 |
| 2021/0279603 | A1 * | 9/2021 | Teran Matus | G06V 20/40 |
| 2022/0383762 | A1 * | 12/2022 | Ali | G08G 5/22 |
| 2023/0285618 | A1 * | 9/2023 | Rosen | A61L 2/10 |

* cited by examiner

VIRTUAL FENCING OF A CONTAMINATED AREA

BACKGROUND

The present invention relates generally to the field of computer data processing, and more particularly to a program using historical and real-time data for predicting or detecting a pathological or chemical incident and determining an effective method of deploying a plurality of unmanned vehicles to form a virtual fence of the unmanned vehicles equipped with decontamination devices around the contaminated area.

Unmanned vehicles (UMV), such as unmanned aerial vehicles (UAV) commonly known as drones, or unmanned ground vehicles (UGV) including wheeled unmanned vehicles and biped or quadruped robots are being widely implemented for many purposes. Some UAVs provide a payload carrying capacity that varies according to the UAV's size. UMVs can be directed remotely or in some cases, can navigate autonomously. UAVs or drones are being used for commercial package delivery, disaster relief, recreation, and other applications. Unmanned vehicles can include a wide range of sensors, such as light detection and ranging sensors (e.g., LiDAR sensors), temperature sensors, compasses, cameras, geo-position sensors (GPS), gyroscopes, and accelerometers along with various microcontrollers and computer processor chips.

SUMMARY

Embodiments of the present provide a computer program, a system, and a method for retrieving historical incident data and real-time data associated with a contaminated site to predict a future incident and to identify a current incident. The computer program evaluates the historical incident data and the real-time data to determine a deployment of a plurality of unmanned vehicles to form a virtual fence around the contaminated site. The computer program determines instructions for the deployment of each of the plurality of unmanned vehicles to form the virtual fence around the contaminated site to prevent the spread of contaminants. The computer program sends the instructions to form the virtual fence to each of the plurality of unmanned vehicles. Furthermore, embodiments of the present invention retrieve real-time data associated with the contaminated site, and based, at least in part, on the real-time data, the computer program determines a second deployment of each of the plurality of unmanned vehicles to form the second virtual fence around the contaminated site.

DETAILED DESCRIPTION

Figure 1B:
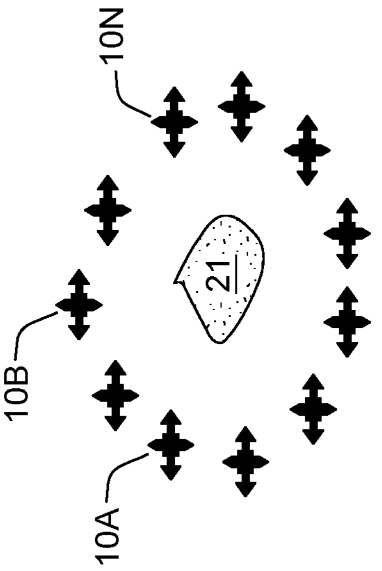
FIG. 1B is an illustration of a second group of unmanned aerial vehicles creating a virtual fence of uniform virtual fence density around a second contamination area, in accordance with at least one embodiment of the invention.

Embodiments of the present invention recognize that areas of contamination may generate illness and be harmful to people, livestock, nearby commercial sites, water supplies, or the environment in general. In some cases, previously contaminated sites, such as garbage dumping areas and previous chemical spill sites are monitored by on-site sensors. Previously contaminated sites may be areas where airborne or waterborne illnesses have erupted from contamination products at the site or may be areas where chemicals spills have occurred. Embodiments of the present invention recognize that unwanted incidents of contagious illnesses or spills of harmful chemicals may occur. An incident may be the release of an unallowable level of any element harmful to people, animals, or the environment such as the release of unallowable levels of pathogens, radiation, or chemicals at a location. Embodiments of the present invention recognize that outbreaks of contagious diseases can occur when pathogens proliferate and spread from refuse dumps or human waste sites. Diseases, such as measles, chickenpox, and coronavirus are contagious airborne illnesses caused by viral pathogens. The airborne germs can be spread by air currents or by living beings exposed to the pathogens. People or animals can spread viruses or other pathogens to adjacent areas or populations by sneezing, coughing, talking, or breathing in the vicinity of another individual. In an ideal world, methods of predicting and containing incidents of disease outbreaks and/or other types of harmful incidents such as chemical spills are desirable.

Embodiments of the present invention provide a method, a computer program, and a computer system for artificial intelligence (AI) enabled incident containment program to predict potential incidences at a previously contaminated site, identify currently occurring incidents, and determine plans to mitigate any predicted or currently occurring incidences using a virtual fence of unmanned vehicles equipped with various decontamination or pathogen eliminating devices. The incident containment program uses an analysis of retrieved historical data on previous outbreaks or incidents to predict potential incidents or outbreaks and provides instructions for the deployment of unmanned vehicles to prevent the predicted incidents. The incident containment program also uses an analysis of real-time data retrieved from IoT feeds (the internet of things feeds) to determine the occurrence of a current incident. Embodiments of the present invention provide an incident containment program that determines a deployment of unmanned vehicles equipped with decontamination and various containment devices including warning devices to create a virtual fence of the unmanned vehicles around a contaminated site of a predicted or current incident. The pathogens or chemicals that are harmful to people, animals, or the environment can be contained or neutralized by one or more decontamination devices such as ultraviolet lights and/or chemicals in the unmanned vehicles forming the virtual fence. Using knowledge-based AI and clustering algorithms, the incident containment program determines the deployment of a fleet of unmanned vehicles to form a virtual fence around the predicted incident or current incident at a contaminated site. The virtual fence of unmanned vehicles surrounds or is over at least a portion of a contaminated site where the incident originated. The incident containment program determines at least a size of the area within the virtual fence of unmanned vehicles, a thickness or density of unmanned vehicles in the virtual fence, a movement of one or more of the unmanned vehicles in the virtual fence, the type and number of unmanned vehicle devices in the virtual fence along with the type of equipment on the unmanned vehicles used to decontaminate or protect the contaminated site.

The incident containment program determines the aspects of the virtual fence (e.g., size, shape, movements, etc.) and the deployment of the unmanned vehicles forming the virtual fence based on the analysis of historical data used to predict a potential incident location and provides instructions for a virtual fence to prevent the predicted incident. Embodiments of the present invention provide the AI enabled incident containment program that determines a deployment of unmanned vehicles and actions by the unmanned vehicles to contain and/or neutralize harmful pathogens or chemicals emitting from a contaminated area based on an analysis of real-time data feeds identifying a current incident that is combined with the analysis of the retrieved historical data of similar types of incidents and/or incidents occurring at the same location or that occurred at a location with similar geological and environmental conditions. The incident containment program provides instructions to the unmanned vehicles to form the virtual fence and to de-contaminate areas around the contaminated site. Embodiments of the present invention provide the incident containment program that uses the real-time and historical incident data to determine if the contaminated area should be protected and provides instructions to protect the contaminated site from unwanted intrusion.

Embodiments of the present invention provide the incident containment program that determines the potential direction of the migration of contaminants, the type of contaminant, a type of action, such as decontamination or isolation of the contaminated area, the number of unmanned vehicles to use in the virtual fence, the placement of each of the unmanned vehicles, the density of the unmanned vehicles in specific areas surrounding the contaminated incident site, the instructions sent to each of the unmanned vehicles forming the virtual fence around the incident, and to send the instructions to the unmanned vehicles and on-site sensors to monitor and send the sensor data used by the program to determine the effectiveness of the deployment of the unmanned vehicles forming the virtual fence.

The present invention will now be described in detail with reference to the Figures. Implementation of embodiments of the invention may take a variety of forms, and exemplary implementation details are discussed subsequently with reference to the Figures. Many modifications to the depicted environment may be made by those skilled in the art without departing from the scope of the invention as recited by the claims.

Figure 1A:
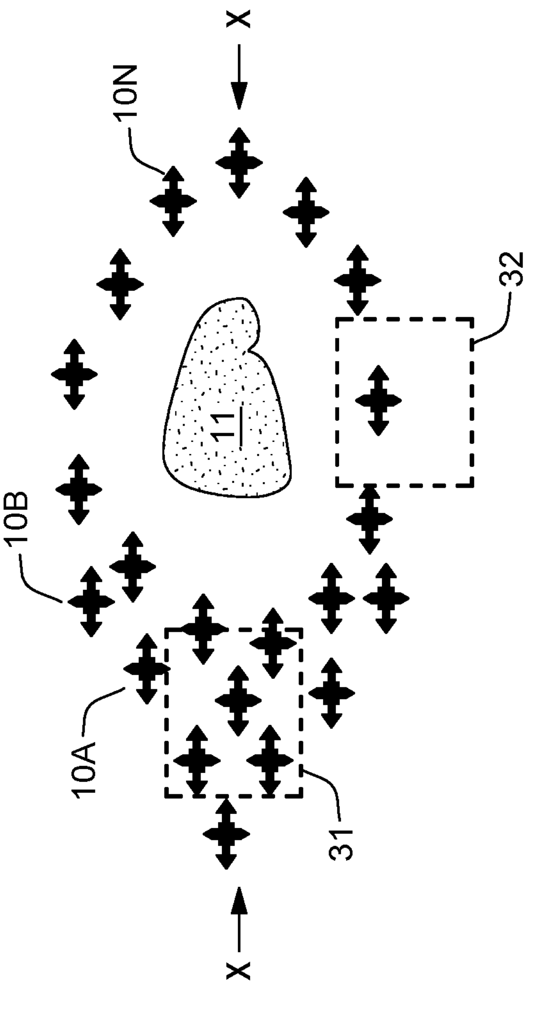
FIG. 1A is an illustration of a first group of unmanned aerial vehicles creating a virtual fence of varying virtual fence density around a first contamination area, in accordance with at least one embodiment of the invention.

FIG. 1A is an illustration of unmanned vehicles (UMV) 10A-10N creating a virtual fence around contaminated area 11, in accordance with at least one embodiment of the invention. As depicted, UMVs 10A-10N are a fleet or a swarm of unmanned vehicles forming a virtual fence of varying fence density around contaminated area 11.

Figure 2:
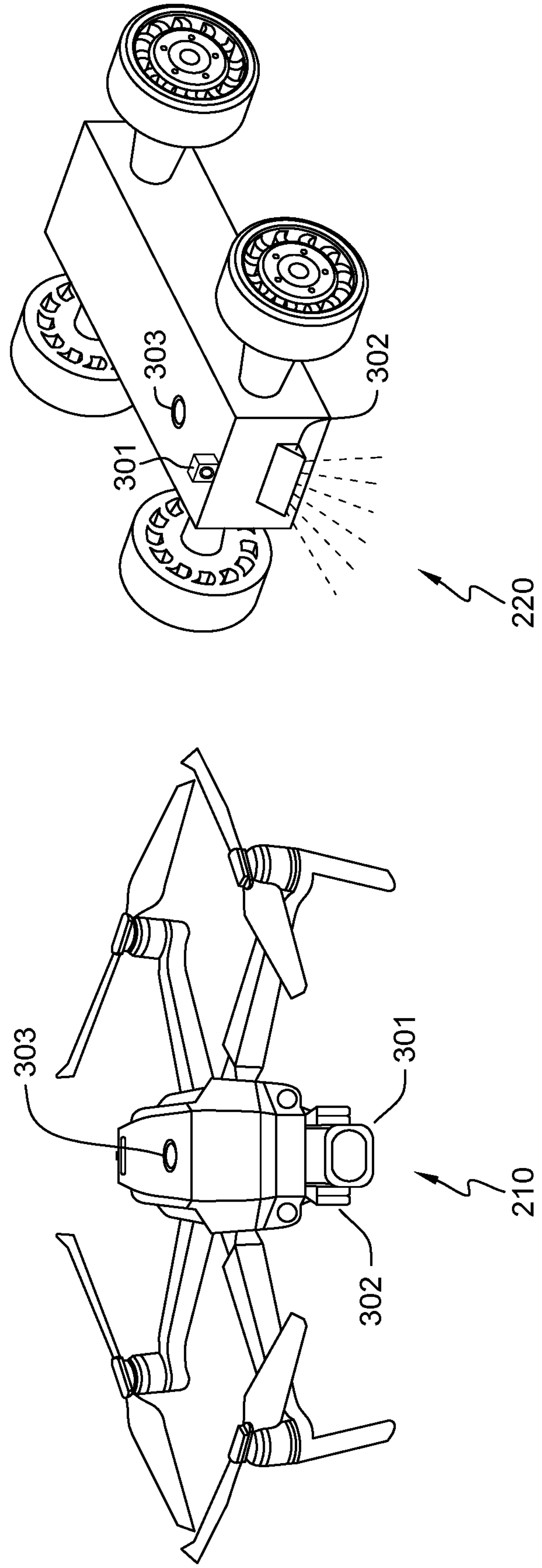
FIG. 2 is an illustration of two representative types of unmanned vehicles used to create a virtual fence around a contamination area, in accordance with at least one embodiment of the invention.

UMV 10A-10N can be any number and any type of unmanned vehicle. For example, UMV 10A-10N can be an unmanned aerial vehicle (UAV), such as a drone. In various embodiments, UMV 10A-10N is any type of drone, such as a large drone capable of carrying large payloads or a small drone equipped with various decontamination devices. UMV 10A-10N are not limited to drones. In some embodiments, UMV 10A-10N are ground unmanned vehicles (UGA), such as a wheeled, a biped, or a four-legged robot. UMV 10A-10N can be any type of unmanned vehicle. Some examples of UMV 10A-10N are depicted in FIG. 2.

Each of UMV 10A-10N include several sensors, communication devices, decontamination devices, processing, and navigation devices. For example, UMV 10A-10N can include at least cameras, temperature sensors, biological and/or chemical sensors, audio devices, decontamination devices, computer microprocessors and/or processors for navigation, communication, and processing sensor data, communication data, and received instructions. In some cases, each of UMV 10A-10N have payload carrying and fluid or dry chemical deposition capability. Additionally, UMV 10A-10N can provide visual communications to people (e.g., flashers, audio messages, digital/LED messages, or flag-like messaging). UMV 10A-10N can include any type of attachment, sensors, or devices available in unmanned vehicles.

Figure 3:
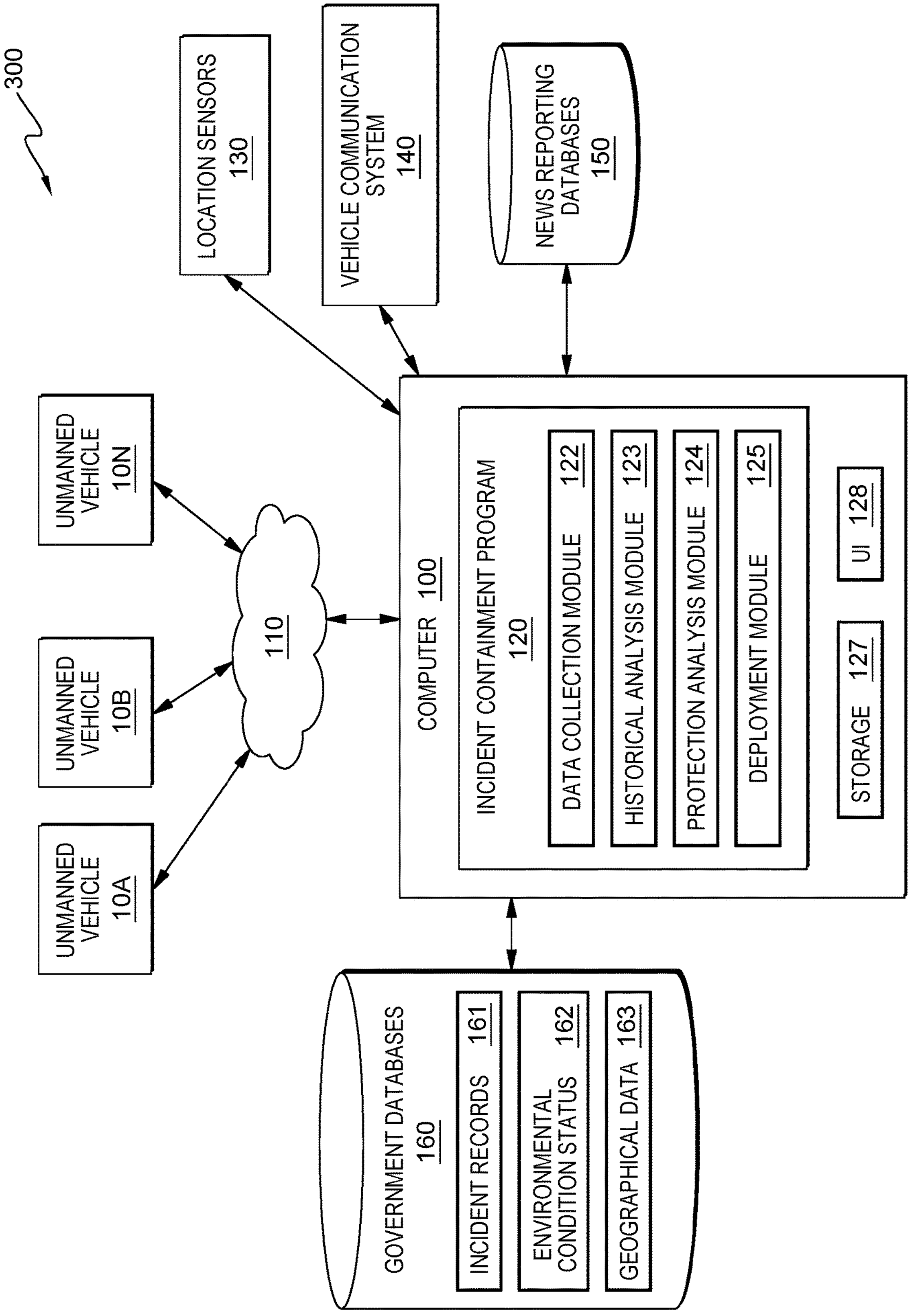
FIG. 3 depicts a functional block diagram of a computing environment suitable for the operation of an incident containment program for deploying unmanned vehicles for virtual fencing of the contaminated area, in accordance with at least one embodiment of the invention.

In various embodiments, an AI-enabled incident containment program, such as incident containment program 120 depicted in FIG. 3, determines the number of UMV 10A-10N, the movement of any of UMV 10A-10N, and the location of each of UMV 10A-10N. For example, as depicted in FIG. 1A, the fleet or swarm of UMV 10A-10N can have varying densities or thicknesses depending on at least the size of contamination area 11, the type of contaminant in contaminated area 11, the weather conditions, the geography, other nearby contaminated areas, and the population in the vicinity of contaminated area 11.

As depicted in FIG. 1A, UMV 10A-10N deployed by the incident containment program form a virtual fence around contaminated area 11 where a larger number of UMV 10A-10N are deployed in area 31 on the left side of contaminated area 11 than in area 32 in the bottom area or in the right side of contaminated area 11. The denser deployment of UMV 10A-10N in some areas of the virtual fence creating a thicker virtual fence around contaminated area 11 may be determined to be necessary by the incident containment program due to a higher population in the vicinity of area 31, or a direction of the airflow or wind moving the contaminates, such as a wind blowing the pathogens or chemicals to the left side of FIG. 1A toward area 31.

In some embodiments, the determination by the incident containment program of a thicker or denser virtual fence of the deployed unmanned vehicles in area 31 is made to identify another contaminated area in the vicinity of contaminated area 11. In these cases, the program determines an increased density of the deployed unmanned vehicles is required in area 31 on the left side of contaminated area 11 which is adjacent to another contaminated area (not depicted in FIG. 1A). As depicted in FIG. 1A, five of UMV 10A-10N are in area 31 while only one UMV 10A-10N resides in area 32 where area 31 and 32 have the same size. The denser deployment of more UMV 10A-10N in area 31 prevents potential cross-contamination between the two contaminated areas.

In other cases, geography, such as mountains, rivers, and valleys are used at least, in part, by the incident containment program to determine the configuration of the deployed UMV 10A-10N forming a virtual fence around contaminated area 11. In another example, the configuration of the deployed UMV 10A-10N is determined, at least in part, by the analysis of any previous incident in the vicinity of contaminated area 11 and/or by the analysis of any previous incident involving a similar pathogen or chemical by the incident containment program.

While FIG. 1A depicts the deployed UMV 10A-10N in an oval-shaped virtual fence, the shape of the virtual fence of UMV 10A-10N can be any shape determined by the incident containment program. For example, the deployed UMV 10A-10N may form a circle, a square, or any regular or irregular shape surrounding contaminated area 11. In some embodiments, UMV 10A-10N de-contaminate the area around contaminated area 11, for example by using infrared, ultraviolet, high-intensity light, ultrasound, laser devices, chemical sprayers, or the like that are integrated into UMV 10A-10N. For example, in the case of germs or viruses originating from contaminated area 11 which is a dump or human waste site, an ultraviolet light-emitting device can eliminate the germs or pathogens. In other examples, a spraying device using a neutralizing chemical can be used to neutralize harmful chemicals or pathogens.

While the swarm or fleet of UMV 10A-10N can be deployed by the incident containment program in a static formation depicted in FIG. 1A, in other embodiments, the fleet of UMV 10A-10N is a moving deployment of UMV 10A-10N. In other words, each UMV 10A-10N is moving together in a defined pattern to form a moving virtual fence. In these embodiments, the virtual fence formed by UMV 10A-10N can change shape, size, and density according to instructions received from the incident containment control program. In some embodiments, selected unmanned vehicles of 10A-10N receive instructions from the incident containment program to move. In one embodiment, the incident containment program depicted in FIG. 3 determines that the virtual fence depicted in FIG. 1A is created using both unmanned aerial vehicles (e.g., drones) and unmanned ground vehicles.

Contaminated area 11 depicted in FIG. 1A can have any shape, size, and/or be composed of any type of pathogen or contaminant. For example, contaminated area 11 can be a waste dumping site capable of generating pathogens, or contaminated area 11 can be a location of a first identified case of a virus or other illness. Contaminated area 11 can be an area predicted by the analysis of historical data of previous incidents and/or can be an area identified by a current event from received or retrieved real-time data. The real-time data can include data from sensors or monitors at the predicted location, a communication from a vehicle such as a police vehicle, a fire vehicle or truck, or an ambulance, or a communication from a government agency, such as the Center for Disease Control and Prevention (i.e., CDC). In some cases, contaminated area 11 is a site of a previous or current chemical spill. Contaminated area 11 may change in shape or size.

In some embodiments, contaminated area 11 is eliminated by UMV 10A-10N based, at least in part, on the analysis and instructions provided by the incident containment program. For example, in some embodiments, the incident containment program determines that UMV 10A-10N should be deployed directly over and around contaminated area 11 using one or more devices, such as infrared emitters or spray to eliminate the pathogens, germs, and/or to neutralize harmful chemicals in contaminated area 11.

FIG. 1B is an illustration of the second group of UMV 10A-10N creating a virtual fence of uniform density around contamination area, 21 in accordance with at least one embodiment of the invention. As depicted in FIG. 1B, contaminated area 21 can be smaller than contaminated area 11 and may have a different shape. In other examples, contaminated area 21 can be the same size and shape as contaminated area 11. Contaminated area 21 like contaminated area 11 may be contaminated with any type of contamination (e.g., any pathogen, waste, or chemicals).

As depicted in FIG. 1B, UMV 10A-10N have been deployed to form a uniform thickness virtual fence around contaminated area 21. For example, a uniform virtual fence may be determined when there is no wind or an even population density around contaminated area 21. The thickness of the uniform virtual fence can be a single UMV 10A-10N thick as depicted in FIG. 1B or can be greater than one UMV 10A-10N thick (e.g., three UMV 10A-10N are stagged or aligned side-by-side around the edges of contaminated area 21). The thickness or the uniform density of the deployed UMV 10A-10N is determined by the incident containment program using the steps discussed later in detail in FIG. 4 and FIG. 5 with respect to the analysis of the historical data and the real-time data FIG. 2 is an illustration of unmanned aerial vehicle (UAV) 210 and unmanned ground vehicle (UGV) 220, in accordance with at least one embodiment of the invention. As depicted, UAV 210 is one example of a drone that can be used in various embodiments of the present invention and UGV 220 is one example of a wheeled robot or an unmanned vehicle that can be used in embodiments of the present invention. While UAV 210 and UGV 220 are examples of unmanned vehicles that can be used as UMV 10A-10N in FIG. 1A and FIG. 1B, however, UMV 10A-10N are not limited to these examples of an unmanned vehicle. For example, UMV 10A-10N can be one or more a multi-legged UGA, or robot or may be any combination of drones, wheeled robots, quadruped robots (e.g., four-legged robots), etc.

UAV 210 and UGV 220 each have at least one digital camera 301 capable of capturing digital images or video, at least one decontamination device 302, and one or more sensors 303. In other examples, the number and location of sensors 303, decontamination device 302, and digital camera 301 may be different. In various embodiments, UAV 210 and UGV 220 can include various microprocessors and computer processors, other devices, and equipment such as containers or small tanks to hold chemicals, arms or similar extensions for picking up and carrying a payload not depicted but used in any type of UMV. For example, not depicted in FIG. 2, UAV 210 and UGV 220 that can be used as UMV 10A-10N in FIGS. 1A and 1B can include an audio device (not depicted), such as a speaker, a siren, a microphone, or a very small bullhorn can also be included in UAV 210 and UGV 220 to provide audible warnings in addition to or instead of decontamination actions using one of decontamination devices 302. For example, the audio devices or banners (not depicted) on UAV 210 and UGV 220 may be used when incident protection program 120 depicted in FIG. 3 determines that the contaminated area should be protected from people entering it.

Decontamination device 302 can be one or more of an infrared device, an ultraviolet light-emitting device, a laser device, an ultrasound device, tank with a dispensing unit or an opening, a spray device, a small container, or any other type of decontamination device. While only one decontamination device 302 is depicted, multiple decontamination devices and/or multiple types of decontamination devices may be on each of UAV 210 and UGV 220. Decontamination device 302 can be instructed by ICP 120 depicted in FIG. 3 to engage or disengage. For example, ICP 120 sends instructions to UAV 210 to turn on the ultraviolet lights (e.g., to turn on one of decontamination devices 302) on each of the deployed UAV 210.

Sensors 303 may be one or more chemical sensors, light sensors, temperature sensors, motion sensors, or another type of environmental sensor in addition to the compasses, gyroscopes, accelerometers, etc. typically present in unmanned vehicles for navigation. In various embodiments, sensors 303 such as a chemical sensor continually monitor the environment in the vicinity of each of UAV 210 and UGV 220. For example, sensors 303 may detect the presence of a harmful chemical. In another example, sensors 303 may be a biological element detection sensor that can identify the presence of a specific virus or other disease. In one embodiment, ICP 120 depicted in FIG. 3 sends instructions to engage or disengage various types of sensors 303 (e.g., chemical sensors, water sensors, biological sensors, air movement sensors, etc.) at different times and for UAV 210 or UGV 220 in different locations. For example, ICP 120 may send instructions to five UAV 210 in the vicinity of a known water source to turn on water sensors. UAV 210 and UGV 220 may have any number of additional devices or features not depicted in FIG. 2 but that are available in unmanned vehicles.

FIG. 3 depicts a functional block diagram of a computing environment 300 suitable for operation of incident containment program 120 for deploying UMV 10A-10N, in accordance with at least one embodiment of the invention. As depicted, FIG. 3 includes any number of unmanned vehicles depicted as UMV 10A-10N, location sensors 130, computer 100 with incident containment program 120 and storage 127, vehicle communications 140, news reporting databases 150, and government databases 160 all connected over network 110.

Network 110 providing connections and communications within computer environment 300 can be, for example, a local area network (LAN), a wide area network (WAN), such as the Internet, a virtual local area network (VLAN), or any combination that can include wired, wireless, or optical connections. In general, network 110 can be any combination of connections and protocols that will support communications between computer 100, location sensors 130, various vehicle communications 140, new reporting database 150, government databases 160, and any other computing devices not depicted in FIG. 3.

Computer 100 is depicted as including incident containment program 120, storage 127, and user interface (UI) 128. In some embodiments, computer 100 can be a computer, a mainframe computer, a server, a desktop computer, a laptop computer, a tablet computer, a netbook computer, or any other programmable electronic computing device capable of receiving, sending, and processing data, and communicating with features and functions of UMV 10A-10N, location sensors 130, news reporting databases 150, and government databases 160 via network 110. In another embodiment, computer 100 represents a computing system utilizing clustered computers and components (e.g., database server computers, application server computers, etc.) that act as a single pool of seamless resources, such as a cloud computing environment when accessed within distributed data processing environment 300. Computer 100 may include internal and external hardware components, as depicted in more detail, and described in FIG. 6.

Incident containment program 120 is depicted as operating on computer 100. In various embodiments, incident containment program 120 is an AI-enabled program. Incident containment program 120, as depicted, includes data collection module 122, historical analysis module 123, protection analysis module 124, and deployment module 125.

Incident containment program (ICP) 120 retrieves and/or receives both historical data and current or real-time data. In various embodiments, ICP 120 collects historical data about a site and about specific types of contamination (e.g., viruses or chemical spills) from but not limited to news reporting databases 150 and government databases 160 including incident records 161. Historical analysis module 123, using AI methods such as knowledge-based approaches or algorithms, analyzes the various historical incidents of viral outbreaks or chemical spills, to predict the likelihood of an incident in the location or another similar location with a similar type of pathogen or spill. For example, ICP 120 using historical analysis module 123 retrieves data on previous incidents. Historical analysis module 123 may group the incident data by location, date, or type of incident or contaminant such as a specific pathogen or virus and may analyze the propagation and travel of the pathogen or chemicals based retrieved data on environmental conditions such as wind direction, wind, temperature, etc. The analysis by historical analysis module 123 are used by ICP 120 to predict a propagation and possible containment actions for future incidents. Historical analysis module 123 also evaluates the effectiveness of the containment or neutralization efforts applied for each incident, for each location, and for each type of incident (e.g., measles outbreak or chemical spill). Historical analysis module 123 may output for each location and each type of incident a recommended approach for the type of containment, the size of a containment area, and a method of delivery for containment (e.g., line-of-sight infrared light, spraying, etc.) based on the historical data analysis.

ICP 120 retrieves and/or receives real-time or recent data on a current incident or on a site predicted to become an incident location using the internet of things (IoT) such as contamination site location sensor data from location sensors 130, unmanned vehicle data from sensors on drones, such as UMV 10A-10B depicted in FIG. 1A, news reports in news reporting databases 150, and information such as current weather conditions from environmental condition status 160 in government databases 160, or geographical data in geographical data 163 in government databases 160 describing the geography in the vicinity of the location of the contamination site predicted or reported. Additionally, incident containment program 120 may receive or retrieve communications on current incidents from vehicle communication devices in vehicle communications 140 provided by ambulances, fire trucks, or police vehicle communications relating to a current incident. In some cases, ICP 120 may receive an alert issued by a governmental agency such as the Center of Disease Prevent and Protection (i.e., the CDC), a local emergency preparedness agency, or the like identifying a new incident or outbreak.

Protection analysis module 124 in ICP 120 retrieves the real-time or current data from data collection module 122 and historical data, incident predictions, and actions determined for predicted incidents from historical analysis module 123 for similar types of incidents and incidents occurring at the same site or in the vicinity of the current incident. Using AI, protection analysis module 124 evaluates all of the collected data relating to a predicted or current incident at a contaminated site and determines a corrective action plan. The corrective action plans can include at least, the type of corrective or containment, an area to be contained and/or neutralized, and a deployment plan for UMV 10A-10N forming the virtual fence around the contaminated site (e.g., the number drones and location of each of the deployed drones or unmanned ground vehicles). In some embodiments, protective analysis module 124 in ICP 120 evaluates the historical and real-time data and determines the virtual fence is needed to protect the contaminated site. In other embodiments, protective analysis module 124 in ICP 120 determines the contaminated site should be both protected from entry (e.g., using audible or visual warnings) and neutralized using the decontamination devices on the unmanned vehicles from the virtual fence. In each of these cases, protective analysis 124 determines an action plan to create the virtual fence of unmanned vehicles.

In some cases, protection analysis module 124 in ICP 120 determines that a virtual fence with unmanned vehicles to keep specific elements, chemicals, or other pathogens from entering a contaminated area. The specific elements, pathogens, or chemicals may be known to combine with elements in the contaminated area to form a more dangerous pathogen or chemical. In other cases, protection analysis module 124 in ICP 120 may determine an audio alert, warning, or carried banner may be required to keep people away from the contaminated area. In these cases, ICP 120 determines to protect the contaminated area and keep people from entering by using audible or written warnings on or from the virtual fence of drones. The onboard sensors or cameras in the drones may be used to determine that a louder audible warning or alert should be used as people or animals continue to approach the contaminated area.

Deployment module 124 communication instructions to the determined number of UMV 1-A-10N (e.g., drones or UGV). The instructions determined by ICP 120 can include the type of actions to be taken such as a drone movement, one or more decontamination steps (e.g., an ultraviolet light sweep of an area), and/or warnings such as audible messages or visual messages provided by the unmanned vehicles to keep people or animals out of the contaminated site.

Additionally, protection analysis module 123 in ICP 120 continually receives or retrieves real-time data and updates from location sensors 130, UMV 10A-10N sensors, news reports, vehicle communications 140, etc. to provide updated or modified instructions for decontamination actions to be taken by UMV 10A-10N. For example, upon retrieving current weather conditions from either a news report or retrieved from the National Weather Service in government databases 160 indicating a change in the wind direction, protection analysis module 123 determines that a virtual fence formed using a fleet of UMV 10A-10N needs a thicker or more dense deployment of unmanned vehicles on the northern side of an incident site and sends instructions to deployment module 125 to alter the configuration of the deployed UMV 10A-10N. In one embodiment, protection module 123 also sends analysis results and/or deployment instructions to storage 127.

Storage 127 is depicted in computer 100. Storage 127 may be any known type of storage and may include one or more databases. Storage 127 may receive, store, and retrieve may store historical analysis outputs, deployment instructions, and other similar data associated with outputs from ICP 120.

UI 128 provides an interface to access the features and functions of computer 100. In some embodiments, UI 128 provides user access to ICP 120 or data in storage 127. UI 128 provides a display of output and input functions for computer 100. UI 250 enables respective users of computer 100 to receive, view, hear, and respond to input, access applications, display content, and perform available functions. UI 128 may be any type of user interface capable of receiving a user's input to a program or a program's output. For example, UI 128 may be a touch screen display, a high-definition display screen, a keyboard, an audio output, an audio recording device with a voice recognition system, etc.

Location sensors 130 can be any number or type of sensors deployed at a predicted location of an incident such as a waste dump by ICP 120 or at a location of a previous incident. Location sensors 130 can include but are not limited to motion sensors, digital recording devices, chemical or biological sensors, and the like. Location sensors 130 can monitor a site of a predicted incident, a current incident, or a prior incident. In some cases, location sensors 130 can send data on changes to a location such as a change composition or quantity of fumes from the site to ICP 120 on computer 100. In various embodiments, ICP 120 periodically polls or retrieves from location sensors 130 any changes to the environment of a predicted, previous, or current site of an incident.

News reporting databases 150 can be one or more databases storing a collection of current and previous new reports. The news reports stored may include a number of details on current or previous incidents or disease outbreaks at or around contaminated sites and reports on chemical spills.

Government databases 160 include any number of government databases including local, state, and national databases. Government databases 160 include at least incident records 161, environmental condition status 162 which can provide current and historical information on weather conditions, earthquakes, and other environmental conditions, and geographical data 163.

Unmanned vehicles 10A, 10B, and 10N are the same as UMV 10A-10N as previously discussed in detail with respect to FIG. 1A and FIG. 1B. Unmanned vehicles 10A, 10B, and 10N can be similar to or the same as unmanned vehicles 210 and 220 as previously depicted in FIG. 2 but are not limited to vehicles depicted in FIG. 23.

Figure 4:
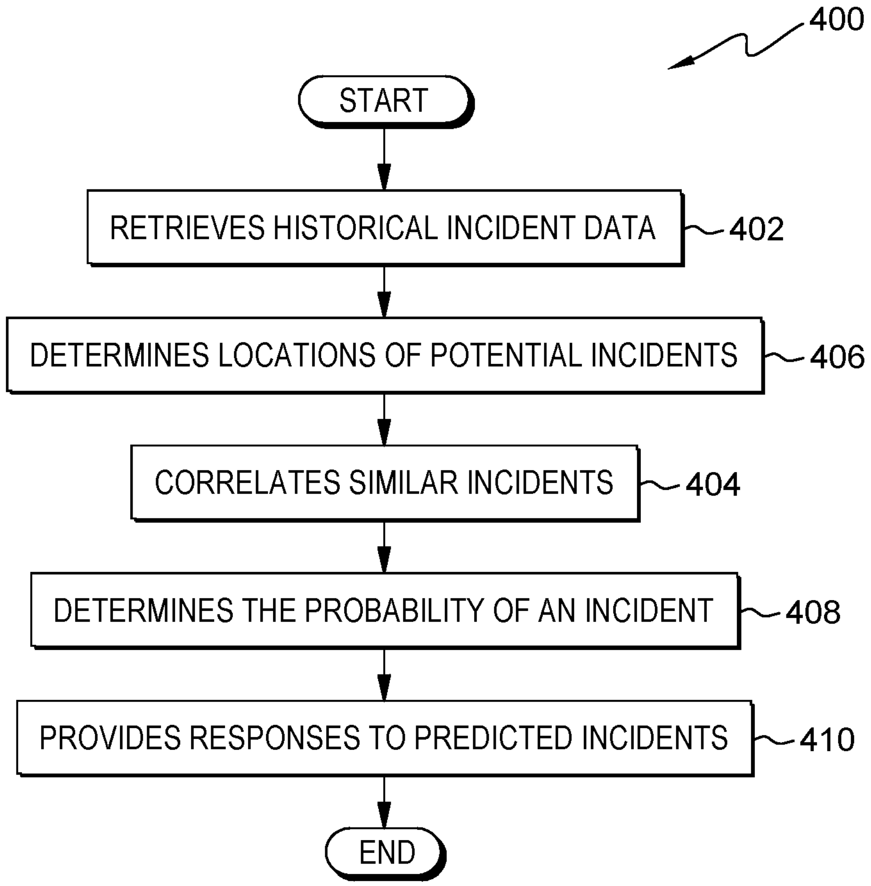
FIG. 4 is an example of a flow chart diagram depicting operational steps for an analysis of historical incident data associated with a current incident by an incident containment program, in accordance with at least one embodiment of the invention.

FIG. 4 is an example of flow chart diagram 400 depicting the operational steps for an analysis of historical incident data by ICP 120 using historical analysis module 123, in accordance with at least one embodiment of the invention. Historical analysis module 123 in ICP 120 retrieves historical data associated with previous incidents to determine the probability of new or re-occurring incidents and evaluates previous incident responses to determine recommended courses of action for various types of incidents potentially occurring at one or more sites.

In step 402, ICP 120 using historical analysis module 123 retrieves historical incident data. ICP 120 with historical analysis module 123 may retrieve information on previous incidents and on previously identified contaminated sites, such as waste dumping sites from one or more of news reporting databases 150 and government databases 160. For example, one or both of news reporting databases 150 and incident records 161 may indicate previous incidents of contaminant-related diseases or chemical spills. ICP 120 may retrieve additional information on geological conditions (e.g., valleys, mountains, streams, etc.) in the vicinity of the incident and weather conditions at the time of the incident from environmental condition status 162 in government databases 160. ICP 120 using historical analysis module 123 may also retrieve from incident records 161 and news reporting databases 150 responses to the incident and the progression and/or the resolution or elimination of the effects of the incident (e.g., elimination or reduction of the spread of a disease or chemicals) at and surrounding the site of the incident.

In step 404, using the retrieved data from step 402, ICP 120 determines the locations of potential incidents. Based on the retrieved historical data, ICP 120 determines the likelihood of a re-occurrence of an incident at a previous location and/or the probability of an incident at an adjacent site or a new location. ICP 120 using historical analysis module 123 identifies previous incident locations, the environment around the previous locations (e.g., geography, commerce, population density, etc.), and the type of incident occurring at each previous incident location. Using a knowledge-based analysis of previous incidents by historical analysis module 123, ICP 120 can predict the likelihood of future incidents at a site of a previous incident. The prediction of future incidents at various locations can include a prediction of the type of incident. The type of incident at a predicted location could include predicting the generation of contagious pathogens from a waste site or an expected chemical in a chemical spill originating from a manufacturing site or a dumping site.

In step 406, ICP 120 correlates similar incidents. Using the retrieved historical data, ICP 120 correlates similar incidents such as outbreaks of a disease or a specific type of chemical spills such as a spill of diesel fuel or hydrochloric acid. For example, by grouping similar incidents (e.g., incidents occurring at a location and/or similar types of incidents) and using clustering algorithms, ICP 120 can classify factors influencing the spread of pathogens or chemicals by analyzing the environmental and geographical parameters associated with each incident to predict the future generation and spread of pathogens at the same or similar locations and/or with similar environmental conditions. The correlation may include an evaluation of corrective actions taken, the weather conditions, the time of year, etc., and the effectiveness of the corrective actions (e.g., how long to neutralize the outbreak or chemicals, how many resources were applied, and for how long, etc.) for each previous incident or location.

In step 408, ICP 120 determines the probability of a new incident. Using the retrieved historical data, the evaluation of potential locations of future potential incidents in step 406, and the correlation of similar incidents, ICP 120 determines the probability of a new incident at a previous incident or a new incident site. ICP 120, using AI and knowledge-based algorithms, predicts potential locations of new incidents and the probability of the new incident based on the analysis of the historical incident data.

In step 410, ICP 120 provides recommended responses to the predicted incidents based on the analysis of the historical data by historical analysis module 123. Utilizing the analysis of the retrieved historical incident data, using clustering algorithms, and applying knowledge-based AI algorithms, ICP 120 determines one or more responses for predicted future incidents. The recommended responses may include a deployment of a number of unmanned vehicles to create a virtual fence around the previously contaminated site. The deployment of the unmanned vehicles can include a type of response such as having the unmanned vehicles spraying an area, using the unmanned vehicles to eliminate a virus using ultraviolet light, and/or using audio alarms on some or all of the unmanned vehicles forming the virtual fence around the contaminated area or incident area. For example, the audio alarms on the unmanned vehicles create a virtual fence to keep people or animals out of the contaminated area (e.g., to protect the contaminated area). The recommended responses may include specific responses to specific weather conditions such as a suitable response when a strong northerly wind is detected, a response for heavy rain and flooding conditions, or a response for no wind, a low population area, and dry conditions. ICP 120 may send the generated recommended responses to storage 127 or another database.

In various embodiments, based on the analysis of the historical data using historical analysis module 123, ICP 120 determines the deployment of unmanned vehicles to the location of a predicted incident to prevent the incident from occurring. For example, ICP 120 determines the number of unmanned vehicles, a type of preventative decontamination (e.g., spray or ultraviolet light), the density of the unmanned vehicles, and the size of the area to be surrounded or covered by the unmanned vehicles. In some cases, ICP 120 determines a different density of unmanned vehicles in a portion of the contaminated area that is adjacent to a stream, another contaminated area, or any other location requiring additional protection from pathogens or chemicals. In some embodiments, ICP 120 creates the instructions to deploy the unmanned vehicles to form a virtual fence around the predicted location of a future incident based on the analysis of the historical data.

Figure 5:
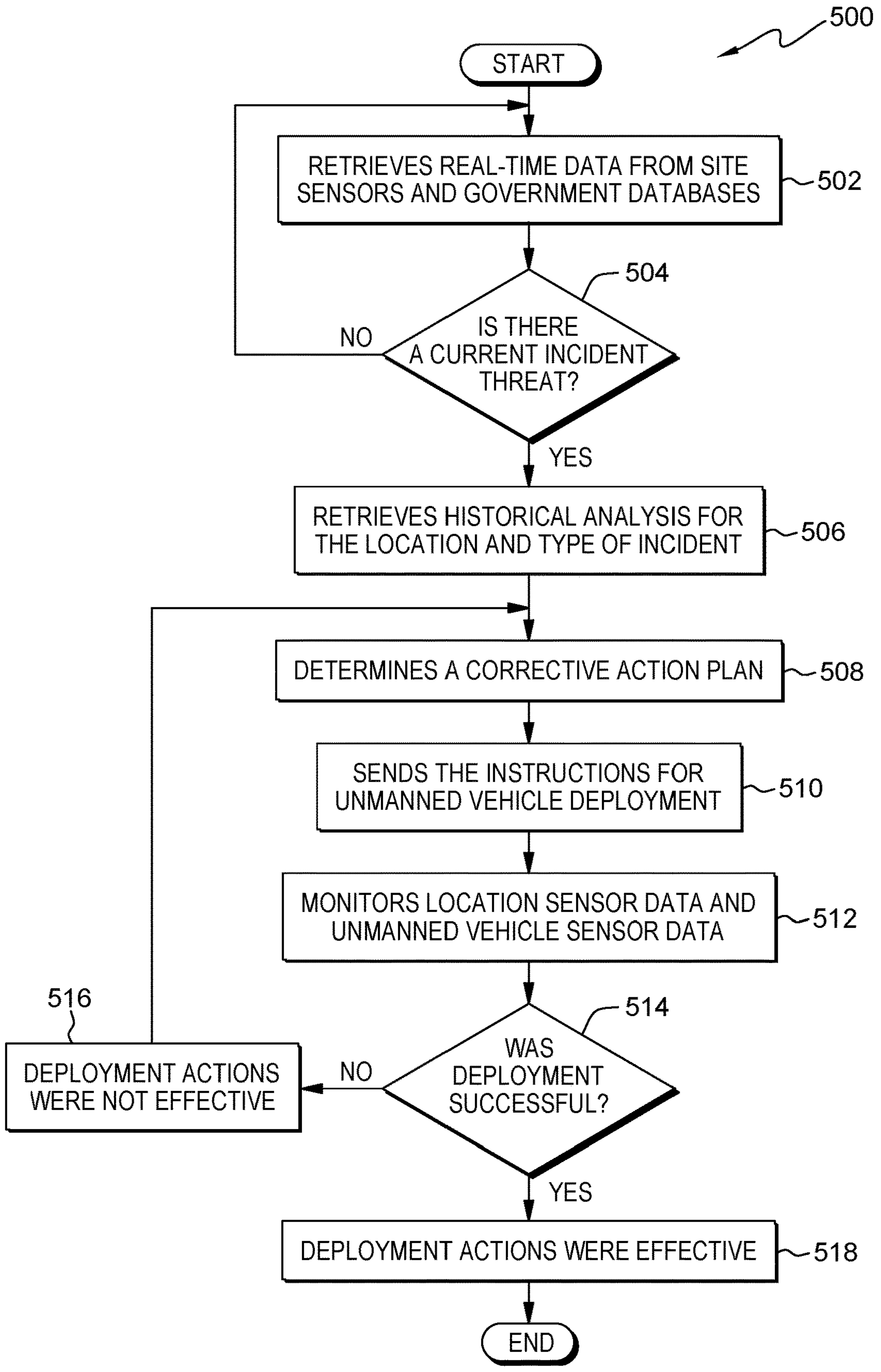
FIG. 5 is an example of a flow chart diagram depicting operational steps for the incident containment program, in accordance with at least one embodiment of the invention.

FIG. 5 is an example of flow chart diagram 500 depicting the operational steps of ICP 120, in accordance with at least one embodiment of the invention. The operational steps of ICP 120 utilize both the historical data analysis previously discussed in detail with respect to FIG. 4 and real-time or current data retrieved or received from various sources such as location sensors 130 or government databases 160 to determine appropriate preventative and corrective actions for an incident occurring due to a contaminated area.

In step 502, ICP 120 retrieves real-time data from on-site or location sensors and government databases. In various embodiments, ICP 120 may also retrieve current or real-time data from news reporting databases, vehicle communications (e.g., police or ambulance reports when appropriate, and other real-time data sources. For example, the real-time or current data retrieved from the location sensors at the contamination site may indicate that no changes have occurred at the location or the retrieved sensor data may indicate an increase in the temperature, increased outgassing, or a change in biological or chemical outputs occurring at the location. The change in biological or chemical outputs from the contaminated site can impact the likelihood or probability of an incident occurring. In some cases, ICP 120 may receive from vehicle communications or location sensors an increased level of the biological or chemical elements being added to the contaminated site. For example, an increase in dumped waste at the location can increase the probability of an incident occurring. In response to increased dumping, ICP 120 may determine an increased number of unmanned vehicles are needed at the location. In another example, vehicle communications, such as ambulance calls, can indicate a sudden emergence of a contagious disease in a neighborhood or a location. The retrieved or received real-time data such as vehicle communications or an emergency report by a government agency released in a government database may indicate the emergence of a contagious disease adjacent to or at a previously contaminated site or at a predicted incident location being monitored.

In decision step 504, ICP 120 determines whether there is a current incident threat. Based, at least in part, on predicted incident location determined by the analysis of historical data and an analysis of the retrieved real-time data, ICP 120 determines if there is a current incident is occurring or if there is a high likelihood of an incident of occurring soon at a location. ICP 120, using an AI enabled analysis, of both real-time data such as on-site sensor data and predicted incident data determines if there is an imminent threat of an incident or a currently occurring incident.

Responsive to determining a current incident is not occurring (no branch of decision step 504), ICP 120 returns to step 502 and continues to retrieve real-time data from location sensors, government databases, and other real-time data sources (e.g., news reporting databases, news data streams, vehicle communications). If there is no change in the location sensor data and if none of the retrieved real-time data such as vehicle communications, incident alerts by a governmental agency, news outlet information streams, or websites identify a currently occurring incident, then ICP 120 determines that there is no current incident threat and/or no increased probability of an incident and returns to monitoring and/or retrieving real-time data in step 502.

Responsive to ICP 120 retrieving or receiving real-time data indicating a change in the location sensor data that identifies the output of large amounts of harmful chemicals or biological elements or retrieves news reports of a disease or chemical spill at the location, then in step 506 (yes branch of decision step 504), ICP 120 retrieves the historical analysis of incidents occurring at the location and the historical data analysis of similar types of incidents (e.g., Ebola outbreaks or oil spills). As previously discussed in detail with respect to FIG. 4, the historical analysis may include recommended actions for the type of incident, or the location based on the evaluations of the previous incident responses. The retrieved historical data can include the area covered by previous contamination at the location, the weather and geological conditions associated with the previous incidents sorted by location and by type of incident.

In step 508, ICP 120 determines a corrective action plan. Using the retrieved analysis of the historical data, the retrieved real-time data from one or more sources (e.g., location sensors, news reports, government databases, etc.), and knowledge-based AI algorithms, ICP 120 determines one or more corrective actions. As previously discussed, using clustering algorithms, ICP 120 can classify which influencing factors such as environmental conditions or geographical aspects are having the biggest impact on the propagation of the pathogens or chemicals. Based on any identified and/or predicted location of an incident (e.g., an identified virus location), and considering environmental parameters (e.g., wind direction, speed, rain, temperature, etc.), ICP 120 predicts the direction of movement of the pathogen or chemicals, a speed of the propagation, determines an effective virtual fence of unmanned vehicles to contain or neutralize the pathogen or chemicals, and/or actions to protect the contaminated site from intrusion. ICP 120 determines the density or thickness of the virtual fence of unmanned vehicles around the contaminated site, a location for each of the unmanned vehicles forming the virtual fence, any movement of each of the unmanned vehicles, any containment actions to prevent pathogen spread, and any decontamination actions to neutralize the pathogens or chemicals emitting from the contaminated site. For example, ICP 120 generates instructions for the unmanned vehicles to use ultraviolet light to remove pathogens under or around each of the unmanned vehicles. In other examples, the unmanned vehicles can use fans to counter the airflow or spray chemicals to neutralize harmful pathogens or other harmful chemicals. In some cases, ICP 120 sends instructions to the unmanned vehicles to use heating elements or lasers to raise temperatures of the air or surfaces under and around the unmanned vehicles to remove the pathogens. In various embodiment, the corrective action plan determined by ICP 120 includes at least a method of containing and/or neutralizing the pathogens and/or chemicals arising from the incident at a contaminated site and a deployment plan for the unmanned vehicles to form a virtual fence around the site (e.g., the number of unmanned vehicles, a location of each of the unmanned vehicles, etc.).

In various embodiments, the method of containing or neutralizing the pathogens or chemicals at a contaminated site includes ICP 120 determining the number of unmanned vehicles to deploy. ICP 120 evaluates the retrieved real-time data and the historical data analysis to determine an area to be surrounded or covered by a virtual fence of unmanned vehicles that may be dispensing or applying one or more decontamination methods. ICP 120 determines the number or density of the unmanned vehicles to contain or decontaminate the area surrounding an incident. In one embodiment, ICP 120 determines that the contamination area is to be covered by the unmanned vehicles for decontamination. In other words, the virtual fence of unmanned vehicles forms a mesh-like deployment of evenly spaced unmanned vehicle covering the contaminated area. In some cases, ICP 120, based on the evaluation of real-time and historical data, may determine different densities of the unmanned vehicles are needed in different locations around or over the contaminated area. In some cases, where a deployment of unmanned vehicles was determined based, on the analysis of the historical data predicting a future incident at the previously contaminated site, ICP 120 may determine a second deployment for a new virtual fence of unmanned vehicles around the contaminated site, based, at least in part, on the real-time data.

In various embodiments, ICP 120, based on the real-time and historical data, determines how many unmanned vehicles are needed in sides of the contaminated area. For example, ICP 120 determines it is important to protect the side of the contaminated area that is adjacent to a river to prevent the potential water-borne spread of pathogens or chemicals. In this case, ICP 120 determines that a high density of unmanned vehicles is needed on the side of the contaminated area adjacent to the river. In another example, ICP 120 determines that two sides of the contaminated area are adjacent to densely populated areas and should be protected by a dense swarm of drones. In this case, ICP 120 may determine that the corrective action plan includes six drones emitting ultraviolet light or a high intensity light are needed on each side of the contaminated area adjacent to the populated area.

In step 510, ICP 120 sends the instructions for the unmanned vehicle deployment to each of the unmanned vehicles or to an unmanned service provider that deploys the unmanned vehicles. The instructions include at least a location for each drone and a type of decontamination or containment method to deploy (e.g., ultraviolet light, a chemical spray, etc.). In some cases, the instructions include a speed and direction for each drone to move so that the swarm or virtual fence each drone can move to a different area to de-contaminate. In this way, more of the area surrounding the contaminated area can be de-contaminated as the drones move together around the contaminated area or site. The instructions from ICP 120 for the unmanned vehicle movement can increase or reduce the area surrounded by the virtual fence. In other cases, the instructions determined and sent by ICP 120 can for specific drones to move. For example, as the on-site sensors or the sensors on the unmanned vehicles detect fewer contaminates or chemicals, ICP 120 sends instructions to reduce the size of the area surrounded by the virtual fence. The instructions are generated and sent wirelessly by ICP 120 to each of the drones or other type of UMV forming the virtual fence.

In step 512, ICP 120 monitors location sensor data and the unmanned vehicle sensor data. ICP 120 retrieves, on a pre-determined schedule or on-demand, location sensor data from location sensors 130 discussed in reference to FIG. 3. One or more sensors, such as cameras or chemical sensors, can be placed in and around the contaminated area based on a prediction on an incident by ICP 120 or based on a current incident that is identified by the real-time data (e.g., IoT data).

As previously discussed, the unmanned vehicles or drones are equipped with various onboard sensors. ICP 120 can send instructions to the drone microcontrollers or processors to monitor the area under the drone every minute, every five minutes, or as otherwise instructed using digital cameras, for example. ICP 120 can also send instructions to each of the drones and/or other type of unmanned vehicle to send the captured sensor data back to ICP 120. In response, the unmanned vehicles or drones will send the sensor data to ICP 120.

In decision step 514, ICP 120 determines whether the deployment was successful. Based on the received or retrieved sensor data from the unmanned vehicles and/or the location sensors, ICP 120 determines if the unmanned vehicle deployment contained and/or eliminated the contamination causing a current incident. In some embodiments, ICP 120 evaluates the real-time data associated with the incident to use in the determination of the success of the virtual fence of the deployed unmanned vehicles.

In step 516, ICP 120 determines that the deployment was not successful (no branch of decision step 514). ICP 120 evaluates the received or retrieved location sensor data and unmanned vehicle sensor data along with any retrieved real-time data from newspapers, vehicle communications, or local, state, or national government databases. For example, when a government database includes a government official's report of a high level of contamination at the site and/or when the location sensors record an increased level of the contamination or a level of contamination is above an allowable level at or around the contaminated site, then ICP 120 determines that the deployment of the unmanned vehicles as required by the corrective action plan was not successful.

In response to determining that the deployment and containment efforts determined by ICP 120 were not successful, then ICP 120 begins another evaluation using the most recent real-time data and the historical data analysis to determine another corrective action plan in step 508. Using the AI-enabled system and the real-time data collected after performing the first and not completely successful unmanned vehicle containment and decontamination effort, ICP 120 returns to step 508 to determine a new corrective action plan to contain and/or eliminate the pathogens or chemicals arising from the contaminated area. ICP 120 will send the instructions generated for the second corrective action plan to the unmanned vehicles. ICP 120 will monitor and retrieve sensor data from the location sensors, the unmanned vehicle sensors, and other real-time data sources to determine if the second corrective action deployment is successful.

In response to determining that the deployment was successful, ICP 120 evaluation of the current incident ends (yes branch 518 of decision step 514). No further action relating to the current incident is required by ICP 120. In some embodiments, ICP 120 based, at least in part on the analysis of the historical and real-time data, determines that on-site or location sensors should remain at the contaminated incident site. In other embodiments, upon determining that the deployment of the unmanned vehicles was successful, ICP 120 sends instructions to the unmanned vehicles to remove the on-site or location sensors (e.g., when a low level or no pathogens are detected). The instructions to remove the sensor can occur when ICP 120 does not predict another incident at the location. For example, based, in at least in part, on the local newspaper reports that undetectable levels of a spilled chemical or a pathogen were recorded by health officials, ICP 120 determines instructions can be provided to one or more of the unmanned vehicles to remove the location sensors and end monitoring of the site.

Figure 6:
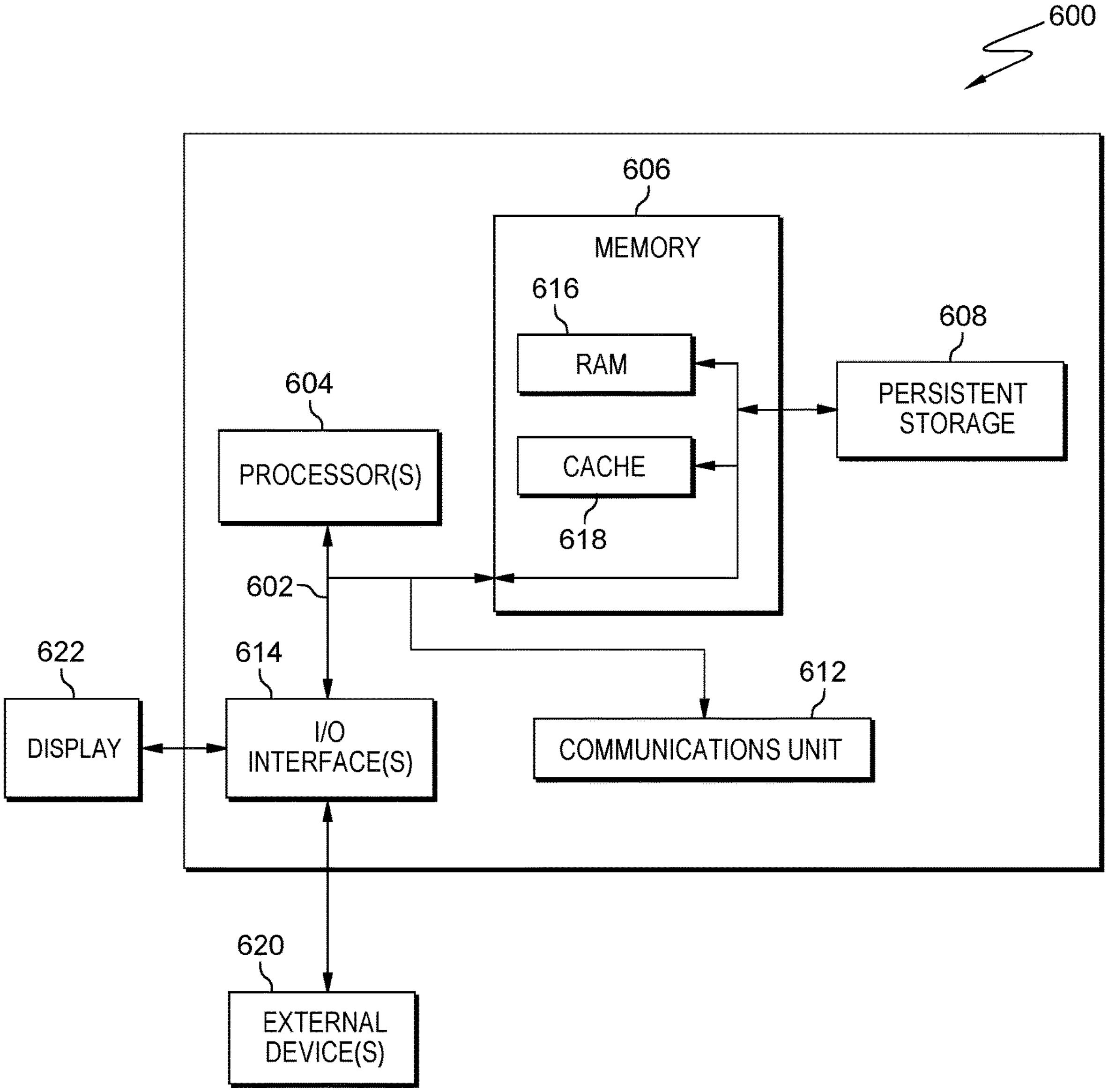
FIG. 6 is a block diagram depicting components of a computer system suitable for executing the incident containment program, in accordance with at least one embodiment of the invention.

FIG. 6 is a block diagram depicting components of a computer system 600 suitable for executing the incident containment program, in accordance with at least one embodiment of the invention. FIG. 6 displays the computer system 600, one or more processor(s) 604 (including one or more computer processors or central processor units), a communications fabric 602, a memory 606 including, a RAM 616, and a cache 618, a persistent storage 608, a communications unit 612, I/O interfaces 614, a display 622, and external devices 620. It should be appreciated that FIG. 6 provides only an illustration of one embodiment and does not imply any limitations with regard to the environments in which different embodiments may be implemented. Many modifications to the depicted environment may be made.

As depicted, the computer system 600 operates over the communications fabric 602, which provides communications between the computer processor(s) 604, memory 606, persistent storage 608, communications unit 612, and input/output (I/O) interface(s) 614. The communications fabric 602 may be implemented with an architecture suitable for passing data or control information between the processors 604 (e.g., microprocessors, communications processors, and network processors), the memory 606, the external devices 620, and any other hardware components within a system. For example, the communications fabric 602 may be implemented with one or more buses.

The memory 606 and persistent storage 608 are computer readable storage media. In the depicted embodiment, the memory 606 comprises a random-access memory (RAM) 616 and a cache 618. In general, the memory 606 may comprise any suitable volatile or non-volatile one or more computer readable storage media.

Program instructions for incident containment program 120 may be stored in the persistent storage 608, or more generally, any computer readable storage media, for execution by one or more of the respective computer processors 604 via one or more memories of the memory 606. In an embodiment, program instructions for incident containment program 120 may be stored in memory 606. The persistent storage 608 may be a magnetic hard disk drive, a solid-state disk drive, a semiconductor storage device, read only memory (ROM), electronically erasable programmable read-only memory (EEPROM), flash memory, or any other computer readable storage media that is capable of storing program instruction or digital information.

The media used by the persistent storage 608 may also be removable. For example, a removable hard drive may be used for persistent storage 608. Other examples include optical and magnetic disks, thumb drives, and smart cards that are inserted into a drive for transfer onto another computer readable storage medium that is also part of the persistent storage 608.

The communications unit 612, in these examples, provides for communications with other data processing systems or devices. In these examples, the communications unit 612 may comprise one or more network interface cards. The communications unit 612 may provide communications through the use of either or both physical and wireless communications links. In the context of some embodiments of the present invention, the source of the various input data may be physically remote to the computer system 600 such that the input data may be received, and the output similarly transmitted via the communications unit 612.

The I/O interface(s) 614 allow for input and output of data with other devices that may operate in conjunction with the computer system 600. For example, the I/O interface 614 may provide a connection to the external devices 620, which may be as a keyboard, keypad, a touch screen, or other suitable input devices. External devices 620 may also include portable computer readable storage media, for example thumb drives, portable optical or magnetic disks, and memory cards. Software and data used to practice embodiments of the present invention may be stored on such portable computer readable storage media and may be loaded onto the persistent storage 608 via the I/O interface(s) 614. The I/O interface(s) 614 may similarly connect to a display 622. The display 622 provides a mechanism to display data to a user and may be, for example, a computer monitor.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disk read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adaptor card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine-dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, though the Internet using an Internet Service Provider). In some embodiments, electronic circuitry including, for example programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram blocks or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of computer program instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method, the computer-implemented method comprising:

retrieving, by one or more computer processors, historical incident data and real-time data associated with a contaminated site;

evaluating, by the one or more computer processors, the historical incident data and the real-time data associated with the contaminated site to predict a future incident at the contaminated site;

determining, by the one or more computer processors, a first deployment of a plurality of unmanned vehicles to form a first virtual fence around the contaminated site based on the predicted future incident, wherein the first deployment of the plurality of unmanned vehicles to form the first virtual fence, wherein the first virtual fence includes a thickness of the virtual fence, wherein the thickness is determined by an amount of population in a vicinity to the contaminated area;

determining, by the one or more computer processors, instructions for the first deployment of each of the plurality of unmanned vehicles to form the first virtual fence around the contaminated site;

sending, by the one or more computer processors, the instructions to form the first virtual fence around the contaminated site to each of the plurality of unmanned vehicles; and removing, by the one or more computer processors, pathogens under the plurality of unmanned vehicles utilizing lasers to raise surface temperature, wherein the pathogens are viral outbreaks.

2. The computer-implemented method of claim 1, wherein evaluating the real-time data and the historical incident data associated with the contaminated site, further comprises:

retrieving, by the one or more computer processors, the real-time data from each of a government database, one or more news reporting databases, and one or more manned vehicles, wherein the manned vehicles include ambulances, fire trucks, and police vehicles;

determining, by the one or more computer processors, a type of pathogen at the contaminated site and a level of an illness outbreak associated with the pathogen at the contaminated site;

determining, by the one or more computer processors, a type of pathogen elimination device associated with removing the pathogen;

determining, by the one or more computer processors, an area around the contamination site to be surrounded by the plurality of unmanned vehicles; and determining, by the one or more computer processors, a location for each unmanned vehicle of the plurality of unmanned vehicles using the pathogen elimination device.

3. The computer-implemented method of claim 2, wherein determining the thickness of the virtual fence on each side of the contamination site, further comprises providing a thicker virtual fence with a higher density of the plurality of unmanned vehicles in the virtual fence adjacent to an area needing additional protection.

4. The computer-implemented method of claim 1, wherein determining the first deployment of the plurality of unmanned vehicles to form the first virtual fence around the contaminated site, further comprises:

determining, by the one or more computer processors, that the contaminated site is adjacent to a second contaminated site;

determining, by the one or more computer processors, to increase the density of the first virtual fence adjacent to the second contaminated sited, wherein the increased density provides a thicker first virtual fence adjacent to the second contaminated site; and sending, by the one or more computer processors, the instructions to deploy more unmanned vehicles to the virtual fence on the side of the contaminated site adjacent to the second contaminated site.

5. The computer-implemented method of claim 4, wherein determining that the contaminated site is adjacent to a second contaminated site, further comprises;

identifying, by the one or more computer processors, at least, a first harmful element at the contaminated site; and identifying, by the one or more computer processors, at least, a second harmful element at the second contaminated site, wherein the increased density of the plurality of unmanned vehicles on the side of the contaminated site that is adjacent to the second contaminated site prevents cross-contamination of the at least one first harmful element and the at least one harmful element.

6. The computer-implemented method of claim 1, wherein the deployment of the plurality of unmanned vehicles to form the first virtual fence around the contaminated site, further comprises:

determining, by the one or more computer processors, that the contaminated site is adjacent to a location requiring additional protection; and sending, by the one or more computer processors, the instructions to deploy more unmanned vehicles to a side of the first virtual fence that is adjacent to the location requiring additional protection.

7. The computer-implemented method of claim 1, wherein determining the first deployment of each of the plurality of unmanned vehicles to form the first virtual fence around the contaminated site, further comprises determining, by the one or more computer processors, a mesh-like deployment of evenly spaced unmanned vehicles of the plurality of unmanned vehicles covering the contaminated site.

8. The computer-implemented method of claim 1, further comprising:

retrieving, by the one or more computer processors, sensor data from each of the plurality of unmanned vehicles;

retrieving, by the one or more computer processors, the sensor data captured by one or more on-site sensors at the contaminated site;

determining, by the one or more computer processors, a level of one or more harmful elements at the contaminated site;

determining, by the one or more computer processors, an unallowable level of the one or more harmful elements is present at the contaminated site; and increasing, by the one or more computer processors, the density of the first virtual fence.

9. The computer-implemented method of claim 8, wherein responsive to determining the unallowable level of the one or more harmful elements is not present at the contaminated site, sending, by the one or more computer processors, instructions to one or more unmanned vehicles of the plurality of unmanned vehicles to remove the one or more on-site sensors.

10. The computer-implemented method of claim 8, wherein increasing the density of the first virtual fence increases the thickness of the first virtual fence.

11. The computer implemented method of claim 1, wherein the plurality of unmanned vehicles are each of an unmanned aerial vehicle or an unmanned ground vehicle equipped with one or more decontamination devices.

12. The computer-implemented method of claim 1, wherein the first deployment of the plurality of unmanned vehicles to form the first virtual fence the first virtual fence, further comprises determining, by the one or more computer processors, one or more different densities of the plurality of unmanned vehicles in different locations over the contaminated site.

13. A computer program product comprising:

one or more computer readable storage media and program instructions collectively stored on the one or more computer readable storage media, the program instructions executable by one or more computer processors, the program instructions comprising instructions for:

retrieving historical incident data and real-time data associated with a contaminated site;

evaluating the historical incident data associated with the contaminated site to predict a future incident at the contaminated site;

determining a first deployment of a plurality of unmanned vehicles to form a first virtual fence around the contaminated site based on the predicted future incident, wherein the first deployment of the plurality of unmanned vehicles to form the first virtual fence, wherein the first virtual fence includes a thickness of the virtual fence, wherein the thickness is determined by an amount of population in a vicinity to the contaminated area;

determining instructions for the first deployment of each of the plurality of unmanned vehicles to form the first virtual fence around the contaminated site;

sending the instructions to form the first virtual fence around the contaminated site to each of the plurality of unmanned vehicles; and removing, by the one or more computer processors, pathogens under the plurality of unmanned vehicles utilizing lasers to raise surface temperature, wherein the pathogens are viral outbreaks.

14. The computer program product of claim 13, wherein evaluating the real-time data and the historical incident data associated with the contaminated site, further comprises:

retrieving the real-time data from each of a government database, one or more news reporting databases, and one or more manned vehicles, wherein the manned vehicles include ambulances, fire trucks, and police vehicles;

determining a type of pathogen at the contamination site and a level of an illness outbreak associated with the pathogen at the contaminated site;

determining an area around the contamination site to be surrounded by the plurality of unmanned vehicles forming the second virtual fence;

determining a type of pathogen elimination device associated with removing the pathogen; and determining a location for each of the plurality of unmanned vehicles using the pathogen elimination device.

15. The computer program product of claim 14, wherein determining the second deployment of the plurality of unmanned vehicles to form the second virtual fence around the contaminated site, further comprises:

determining that the contaminated site is adjacent to a second contaminated site; determining, by the one or more computer processors, wherein the increased density provides a thicker first virtual fence adjacent to the second contaminated site; and sending the instructions to deploy more unmanned vehicles to a side of the second virtual fence around the contaminated site that is adjacent to the second contaminated site.

16. The computer program product of claim 13, wherein determining the first deployment of the plurality of unmanned vehicles to form the first virtual fence around the contaminated site, further comprises:

determining that the contaminated site is adjacent to a second contaminated site; and sending the instructions to deploy more unmanned vehicles to a side of the virtual fence around the contaminated site that is adjacent to the second contaminated site.

17. The computer program product of claim 13, further comprising:

retrieving sensor data from each of the plurality of unmanned vehicles;

retrieving sensor data captured by one or more on-site sensors at the contaminated site;

determining a level of one or more harmful elements at the contaminated site; and determining whether an unallowable level of one or more harmful elements are present around the contaminated site; and increasing, by the one or more computer processors, the density of the first virtual fence.

18. The computer program product of claim 13, wherein determining the first deployment of each of the plurality of unmanned vehicles to form the first virtual fence around the contaminated site, further comprises determining a mesh-like deployment of evenly spaced unmanned vehicles of the plurality of unmanned vehicles covering the contaminated site.

19. A computer system comprising:
one or more computer processors;
one or more computer readable storage media;
program instructions stored on the one or more computer readable storage media for execution by at least one of the one or more processors, the program instructions comprising instructions to perform:
retrieving historical incident data and real-time data associated with a contaminated site;
evaluating the historical incident data associated with the contaminated site to predict a future incident at the contaminated site;
determining a first deployment of a plurality of unmanned vehicles to form a first virtual fence around the contaminated site based on the predicted future incident, wherein the first deployment of the plurality of unmanned vehicles to form the first virtual fence, wherein the first virtual fence includes a thickness of the virtual fence, wherein the thickness is determined by an amount of population in a vicinity to the contaminated area;
determining instructions for the first deployment of each of the plurality of unmanned vehicles to form the first virtual fence around the contaminated site;
sending the instructions to form the first virtual fence around the contaminated site to each of the plurality of unmanned vehicles; and
removing, by the one or more computer processors, pathogens under the plurality of unmanned vehicles utilizing lasers to raise surface temperature, wherein the pathogens are viral outbreaks.

20. The computer system of claim 19, wherein determining the deployment of the plurality of unmanned vehicles to form the first virtual fence around the contaminated site, further comprises:
determining that the contaminated site is adjacent to a second contaminated site; and
sending the instructions to deploy more unmanned vehicles to a side of the virtual fence around the contaminated site that is adjacent to another contaminated site.

* * * * *